United States Patent [19]

Sugasawa

[11] 4,031,098

[45] June 21, 1977

[54] CAMPTOTHECIN ANALOGUES

[75] Inventor: Tsutomu Sugasawa, Kobe, Japan

[73] Assignee: Shionogi & Co., Ltd., Japan

[22] Filed: Jan. 5, 1976

[21] Appl. No.: 646,596

[30] Foreign Application Priority Data

Feb. 20, 1975 Japan .............................. 50-21359

[52] U.S. Cl. ............................ 260/287 C; 424/258
[51] Int. Cl.$^2$ ...................................... C07D 491/22
[58] Field of Search ............................... 260/287 C

[56] References Cited
UNITED STATES PATENTS 3,894,029  7/1975  Winterfeldt et al. .......... 260/287 C

FOREIGN PATENTS OR APPLICATIONS 2,150,234  4/1973  Germany

*Primary Examiner*—Donald G. Daus
*Assistant Examiner*—David E. Wheeler
*Attorney, Agent, or Firm*—Wenderoth, Lind & Ponack

[57] ABSTRACT

Camptothecin analogues showing more potent antitumor activity than a naturally occurring alkaloid camptothecin, which also exhibit an immunosuppressive activity, in which the 1-ethyl of camptothecin is replaced by various members of substitutents such as alkyls (except ethyl), alkenyls, alkynyls, aralkyls or aryloylalkyls; being produced from readily accessible starting materials on totally synthetic method newly developed by the present inventor.

4 Claims, No Drawings

CAMPTOTHECIN ANALOGUES

The present invention relates to camptothecin analogues. More particularly, it relates to novel camptothecin analogues showing potent anti-tumor and immunosuppressive activities, and to a process for producing them. Said camptothecin analogues may be represented by the following general formula (I):

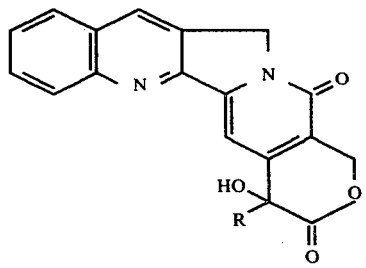

(wherein R is a lower alkyl of 3 – 6 carbon atoms, a lower alkenyl of 3 – 5 carbon atoms, a lower alkynyl of 2 – 3 carbon atoms, an aralkyl of 7 – 8 carbon atoms, or an aryloylalkyl of 8 – 10 carbon atoms).

Camptothecin is an alkaloid isolated from the stem wood of the Chinese tree, *Camptotheca acuminata* Decsne.(Nyssaceae), of which the structure may be represented by the formula (I: $R=CH_2CH_3$). This alkaloid is known to have anti-leukemic and antitumor activities in animals [Wall et al., J.Am.Chem.Soc., 88, 3888 (1966)]. Several synthetic routes to camptothecin by total syntheses have been published by many investigators [A. G. Schultz, Chem.Rev., 73, 385 (1973); G. Stork et al., J.Am.Chem.Soc., 93, 4074 (1971); M. Shamma et al., J.Pharm.Sci., 63 163 (1974); R. Volkmann et al., J.Am.Chem.Soc., 93, 5576 (1971); E. Winterfeld et al., Angew.Chem., 84, 265 (1972); M. Wall, J.Am.Chem.Soc., 94, 3631 (1972); T. Sugasawa et al., Tetrahedron Letters, 1972, 5109; H. Rapoport et al., J.Am.Chem.Soc., 94, 8615 (1972)], but there is no report regarding to camptothecin analogues of the type as mentioned above [Some papers regarding to other types of camptothecin analogues have been published; e.g., S. Danishefsky and S. J. Etheredge, J.Org.Chem., 39, 3430 (1974); J. J. Plattner et al., J.Org.Chem. 39 303 (1974); J. A. Bristol et al., J.Med.Chem., 18, 535 (1975)]. The present inventor has succeeded in developing a new process by which various kinds of camptothecin analogues can be produced in good yield, in which the 1-ethyl of camptothecin is replaced by a wide variety of substituents. Moreover, it has been elucidated that the resultant camptothecin analogues show more potent anti-tumor action than camptothecin itself. The present invention is based on these facts.

The process of this invention may be explained as follows by the general formulae illustrated below; that is, treating compounds of the general formula (II) with a base to yield compounds of the general formula (III) (1st step), reacting the latter with a reagent of the general formula RX to yield compounds of the general formula (IV) (2nd step), permitting the latter to decarboxylation and protecting group removing reaction to yield compounds of the general formula (V) (3rd step), permitting the latter to oxidation to yield compounds of the general formula (VI) (4th step), and permitting the latter to dehydrogenation to yield compounds of the general formula (I) (5th step).

The starting compounds (II) used in this invention, i.e. 5-formyl-8-hydroxymethyl-9-oxo-5,5a,9,11,11a,12-hexahydroindolizino[1,2-b]quinoline-7-malonic acid alkyl esters (hereinafter referred to as malonic acid derivatives) are known compounds which serve as intermediates in the total synthesis of camptothecin disclosed in the specification of Japanese Unexamined publication No. 49/117499.

In the general formulae (I – VI) illustrated above and below, the symbols R, R' and R" each represents the following meaning. R is a lower alkyl of 3 – 6 carbon atoms, e.g. n-propyl, i-propyl, n-butyl, s-butyl, n-pentyl, n-hexyl, etc., a lower alkenyl of 3 – 5 carbon atoms, e.g. allyl, isopropenyl, 2-butenyl, 2-pentenyl, etc., a lower alkynyl of 2 – 3 carbon atoms, e.g. ethynyl, propargyl, etc., an aralkyl of 7 – 8 carbon atoms, e.g. benzyl, phenethyl, etc., or an aryloylalkyl of 8 – 10 carbon atoms, e.g. phenacyl, etc. R' is a lower alkyl of 1 – 4 carbon atoms, e.g. methyl, ethyl, i-propyl, t-butyl, etc. R" is an N-protecting group to quinoline ring, e.g. formyl, acetyl, benzoyl, t-butoxycarbonyl, etc. In the reagent R-X used in the 2nd step, X represents a leaving group, for example, halogen, e.g. iodine, bromine, chlorine, a sulfonyl group, e.g. tosyl, mesyl, etc.

Each step of the reaction in this invention may be carried out as follows.

FIRST STEP

The starting malonic acid derivatives (II) are treated with a base in order to form a lactone ring between one of the 7-malonic esters and the 8-hydroxymethyl of indolizino[1,2-b]-quinoline, yielding the lactone-carboxylic esters (III). As for the base, alkali metal hydroxides such as lithium hydroxide, sodium hydroxide, potassium hydroxide, and the like may preferably be used. Alternatively, other alkali metal bases, for example, alkali metal hydrides, amides, alkoxides, etc., may be used. In carrying out the reaction, it is desirable to use a proper solvent, for example, an alcohol (methanol, ethanol, t-butanol, etc.), an ether (tetrahydrofuran, dioxane, 1,2-dimethoxyethane, etc.), dimethylformamide, dimethylsulfoxide, or the like, according to the base to be used. If required, for example, when an alkali metal hydroxide is used, a small quantity of water may be added. The reaction usually terminates within a period of several minutes or several ten minutes at room temperature.

SECOND STEP

The lactone-carboxylic esters (III) prepared in the preceding step is permitted to reaction with a reagent of the general formula RX to yield mono-substituted derivatives of the general formula (IV). The reaction of this step may be effected according to a condition for the so-called alkylation of active methylenes which is generally carried out in the presence of a base. Examples of the reagents represented by RX are propyl chloride, allyl bromide, isopropenyl chloride, propargyl bromide, benzyl bromide, phenethyl chloride, phenacyl bromide, 1-tosyloxypropane, and the like. As for the base, carbonates such as sodium carbonate, potassium carbonate, etc., hydroxides such as sodium hydroxide, potassium hydroxide, etc., alkoxides such as sodium methoxide, sodium ethoxide, potassium t-butoxide, etc., hydrides such as lithium hydride, sodium hydride, potassium hydride, etc., amides such as lithium amide, sodium amide, diethylaminolithium, etc., and other bases used in the alkylation of active methylenes may be used. The reaction solvent may properly be selected according to the property of base to be used; such solvents involve aromatic solvents, e.g. benzene, toluene, etc., ethers, e.g. tetrahydrofuran, 1,2-dimethoxyethane, etc., ketones, e.g. acetone, methyl ethyl ketone, etc., alcohols, e.g. methanol, ethanol, t-butanol, etc., liquid ammonia, dimethylformamide, and dimethylsulfoxide. The reaction time and temperature also depend on the property of base to be used. In this invention, it is appropriate to use a relatively weak base such as alkali carbonates in order to obtain good result.

THIRD STEP

In this step, the 1-carboxylic esters of monosubstituted derivatives (IV) prepared in the preceding step are permitted to decarboxylation, and concurrently or subsequently the 13-protecting group is removed. The reaction of this step is readily effected by treatment with a mineral acid, for example, hydrochloric acid at room temperaature.

FOURTH STEP

The decarboxylated derivatives (V) prepared in the preceding step are oxidized to yield the hydroxy derivatives (VI) in which the hydroxyl group is introduced into the root of 1-substituent R. The reaction may be carried out by dissolving the compound (V) in a proper solvent and introducing therein oxygen or an oxygen-containing gas, e.g. air, in the presence of a catalyst. As for the catalyst, a strong base such as sodium hydride, potassium t-butoxide, etc., an organic base such as triethylamine, or a bivalent copper compound such as cupric acetate, cupric chloride, etc., may preferably be used. As for the proper solvents, alcohols such as methanol, ethanol, propanol, t-butanol, ethylene glycol, etc., dimethylformamide, dimethylsulfoxide, and mixtures of them may be used. The reaction usually terminates within a period of several 10 minutes or several hours under ice-cooling or at room temperature.

FIFTH STEP

The hydroxy derivatives (VI) prepared in the preceding step are permitted to dehydrogenation to yield the finally objective compounds (I). As for the dehydrogenating agents, benzoquinones such as dichlorodicyanobenzoquinone (DDQ), chloranil, etc., palladium, and selenium dioxide may be used. The reaction may be effected according to the heretofore known methods using these reagents. For example, when DDQ is used as a dehydrogenating agent, the reaction may be carried out by dissolving the starting hydroxy derivative (VI) in a proper solvent, e.g. benzene, toluene, dioxane, t-butanol, adding thereto a proper amount of DDQ, and heating the mixture under refluxing for a period of several 10 minutes or several hours.

The product prepared in each step mentioned above may be used in the subsequent step after isolation and purification in every step or immediately after the reaction termination. The isolation and purification of the product in every step may be effected in a chemically conventional manner, for example, extraction, recrystallization.

ACTION AGAINST LEUKEMIA L-1210

Fifteen thousand pieces of Leukemia L-1210 cells are intraperitoneally inoculated to a group of (C 57 BL × DBA/2)$F_1$ family mice of 16 – 18 g body weight. After the lapse of 24 hours, each test compound is intraperitoneally injected, and the number of survival days are observed. Increase in lifespan over control (ILS) may be calculated as the ratio of average survival days of the group of control mice to that of the group of treated mice. To the group of contol mice, 10% ethanol (0.1 ml/mouse) is intraperitoneally administered. ILS = [(Average survival days of the group of treated mice − Average survival days of the group of control mice) ÷ Average survival days of the group of control mice] × 100.

The following table I indicates the result of the test. The column of "Survivors over 30 days" means the number of survivors (numerator) to the number of mice employed (denominator).

Table I

| Test Compound 1 : R | Dose (mg/kg) | ILS | Survivors over 30 days |
|---|---|---|---|
| $CH_2CH=CH_2$ | 10 | >244 | 7/9 |
|  | 25 | >245 | 8/9 |
| $CH_2C\equiv CH$ | 10 | >117 | 2/8 |
|  | 25 | >149 | 2/8 |
| $CH_2-Ph$ | 10 | >171 | 3/8 |

The compounds (I) prepared in this invention also exhibit remarkably an immunosuppressive activity in addition to the aforementioned anti-tumor activity. The immunosuppressive activity of the compounds (I) was compared with that of a commercially available immunosuppressive agent, cyclophosphamide. Table II indicates the results of test.

TEST METHOD

To a group of ICR female mice, sheep red blood cells ($10^8$/mouse) were intraperitoneally injected for immunization. Test compounds were also intraperitoneally administered at the time of immunization, and their antisera were separated. Hemagglutination titer of the antisera was measured according to the microtiter method, and expressed as $log_2$ reciprocals of the end point dilution. The antibody resistant to 2-mercaptoethanol was determined similarly after treating the separated antisera with 0.1M 2-mercaptoethanol.

Table II

| Test Compound (Dose mg/kg) | Serum antibody titer (-$log^2$ Titer) | | | |
|---|---|---|---|---|
|  | Day 4 | | Day 7 | |
|  | Total | 2ME-resist. | Total | 2ME-resist. |
| Control | 6.5±0.2 | 1.5+0.5 | 6.8±0.2 | 5.5  0.4 |
| (I) R=$CH_2CH=CH_2$ | 3.6±0.8 | 0 | 4.6±0.4 | 1.2±0.4 |
| Cyclophosphamide (70 mg/kg) | 1.2±0.5 | 0 | 6.7±0.6 | 5.3±0.6 |

The result indicates the effect of the compounds (I) is milder on Day 4 but lasting longer than that of cyclophosphamide.

The compounds (I) produced in this invention can be administered alone or in combination with pharmaceutically acceptable carriers, the choice of which depends on the preferred route of administration, solubility of the materials, and pharmaceutical practice. In general, the compounds (I) may be administered in single or divided doses containing from 100 mg to 1000 mg of the active ingredient. Practical examples of pharmaceutical preparations with the compounds (I) are tablets, capsules, pills, suspensions, emulsions, solutions, suppositories, ointments, granules, and powders.

The invention will be better explained by the following example which is not intended as a limitation thereof.

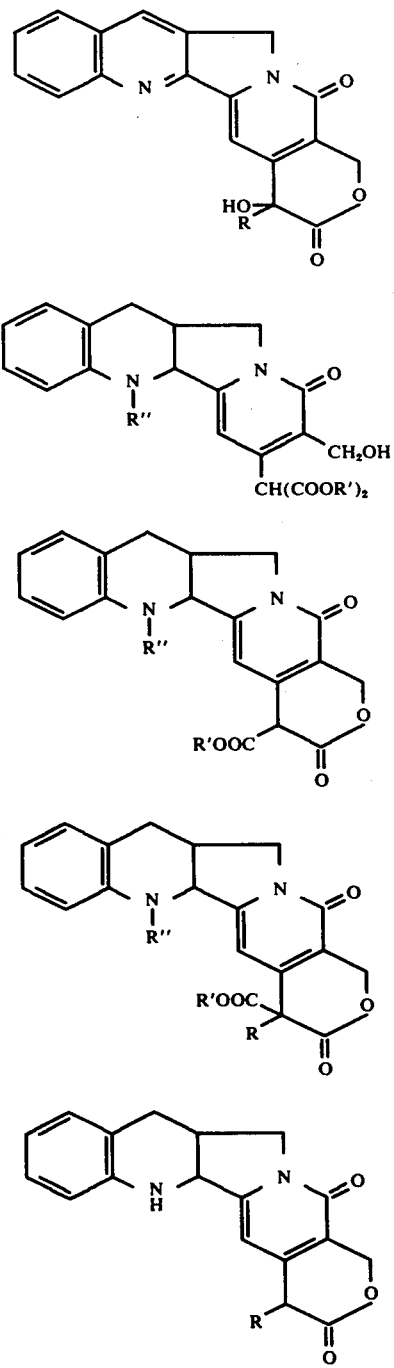

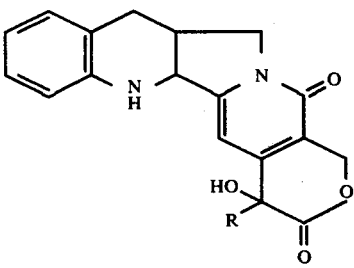

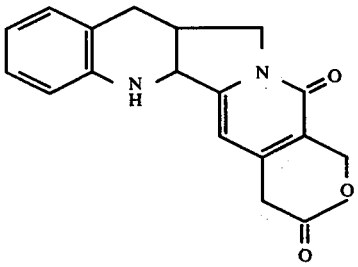

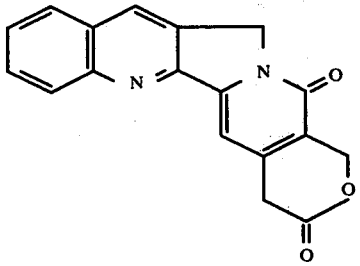

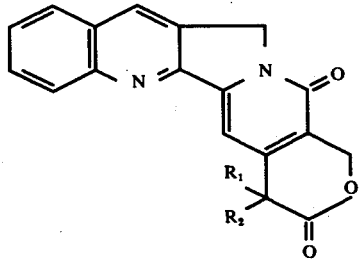

EXAMPLE

1. To a suspension of 500 mg of the malonic acid derivative (II: R' = t-Bu; R" = CHO; t-butyl 5-formyl-8-hydroxymethyl-9-oxo-5,5a,9,11,11a,12-hexahydroindolizino[1,2-b]quinoline-7-malonate) in 9.0 ml of t-butanol is added 1.0 ml of 10% of potassium hydroxide with stirring at room temperature. The reaction mixture gives a solution within 5 minutes, which then becomes muddy again. After 30 minutes, ice-water is added, and the mixture is extracted with chloroform. The extract is washed with water, dried and evaporated to dryness, and the residue is recrystallized from methanol to give 417 mg of the lactonecarboxylic ester (III: R' = t-Bu; R" = CHO; t-butyl 13-formyl-2,5-dioxo-1,2,5,7,7a,8,13,13a-octahydro-4H-pyrano[3,4-f]indolizino[1,2-b]quinoline-1-carboxylate). mp. 257° – 258° C (decomposition). IR: $\nu_{max}^{CHCl}$ 1750, 1730, 1640 cm$^{-1}$. Anal. Calcd. for $C_{24}H_{24}O_6N$ (%): C, 66.04; H, 5.54; O, 22.00; N, 6.42. Found (%): C, 66.14; H, 5.45; O, 21.76; N, 6.35.

2. A suspension of 400 mg of the aforementioned lactonecarboxylic ester (III), 506 mg of potassium carbonate, 222 mg of allyl bromide and 30 ml of acetone is heated under refluxing with stirring in nitrogen atmosphere for 16 hours. After cooling, the reaction mixture is poured onto ice - acetic acid and extracted with a mixture of chloroform and methanol (3 : 1). The extract is washed with water, dried and evaporated to dryness to give 467 mg of the allyl derivative (IV: R = $CH_2CH=CH_2$; R' = t-Bu; R" = CHO; t-butyl 1-allyl-13-formyl-2,5-dioxo-1,2,5,7,7a,8,13,13a-octahydro-4H-pyrano[3,4-f]indolizino[1,2-b]-quinoline-1-carboxylate).

3. A mixture of 467 mg of the aforementioned allyl derivative (IV) with 1 ml of conc. hydrochloric acid is allowed to stand at room temperature for 16 hours. The reaction mixture is admixed with ice and sodium acetate, and extracted with chloroform. The extract is washed with water, dried and evaporated to dryness to give 319 mg of the decarboxylated derivative (V: R = $CH_2-CH=CH_2$; 1-allyl-1,2,5,7,7a,8,13,13a-octahydro-4H-pyrano[3,4-f]indolizino[1,2-b]quinoline-2,5-dione).

4. The aforementioned decarboxylated derivative (V) (319 mg) is dissolved in 25 ml of methanol, and 37 mg of cupric acetate [$Cu(CH_3CO_2)_2 \cdot H_2O$] and 185 mg of triethylamine are added thereto. Then, oxygen gas is introduced to the solution under ice-cooling for 40 minutes. A small quantity of insoluble material is removed by filtration, the solvent is distilled off, and the residue is admixed with ice - acetic acid and extracted with chloroform. The extract is washed with water, dried and evaporated to give 359 mg of the hydroxy derivative (VI: R = $CH_2CH=CH_2$; 1-allyl-1-hydroxy-1,2,5,7,7a,8,13,13a-octahydro-4H-pyrano[3,4-f]indolizino[1,2-b]quinoline-2,5-dione).

5. The aforementioned hydroxy derivative (VI) (359 mg) is dissolved in 30 ml of dioxane containing 460 mg of DDQ and heated under refluxing for 30 minutes. After removal of dioxane by distilliation, the residue is suspended in 1% methanol - chloroform and passed through a column of 25 g of silica gel. The fraction eluated with the same solvent system is recrystallized from methanol to give 100 mg of the camptothecin allyl analogue (I: R = $CH_2CH=CH_2$; 1-allyl-1-hydroxy-1,2,5,7-tetrahydro-4H-pyrano[3,4-f]indolizino[1,2-b]quinoline-2,5-dione). mp. 276° – 278° C (decomposition). IR; $\nu_{max}^{KBr}$ 3315, 1755, 1650 cm$^{-1}$. NMR: δ ($CDCl_3-CF_3COOH$) ppm 2.5 – 2.7 (2H, allyl-H), 4.9 – 5.7 (7H, alicyclic and vinyl-H), 8.0 – 9.1 (6H, aromatic H). Mass: m/e 360 (M$^+$). Anal. Calcd. for $C_{21}H_{16}O_4N_2$ (%): C, 69.99; H, 4.48; O, 17.76; N, 7.77. Found (%): C, 69.77; H, 4.20; O, 17.84; N, 8.03.

The sodium salt: mp.>270° C. IR: $\nu_{max}^{KBr}$ 3400 (broad), 1640, 1600 (broad) cm$^{-1}$.

In the same manner as mentioned above, the following compounds are produced.

1-Hydroxy-1-propargyl-1,2,5,7-tetrahydro-4H-pyrano[3,4-f]indolizino[1,2-b]quinoline-2,5-dione (I: R = $CH_2-C\equiv CH$), mp. 266° – 267° C (decomposition; recrystallized from chloroform - methanol).

1-Benzyl-1-hydroxy-1,2,5,7-tetrahydro-4H-pyrano[3,4-f]indolizino[1,2-b]quinoline-2,5-dione (I: R = $CH_2Ph$), mp. 275° – 276° C (decomposition; recrystallized from methanol).

1-Hydroxy-1-phenacyl-1,2,5,7-tetrahydro-4H-pyrano[3,4-f]indolizino[1,2-b]quinoline-2,5-dione (I: R = $CH_2COPh$), mp. 267° – 268° C (decomposition; recrystallized from chloroform - methanol).

We claim;

1. A compound of the formula:

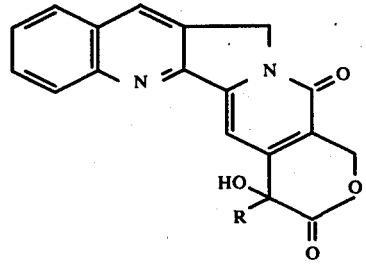

wherein R is allyl, propargyl or benzyl.

2. A compound as claimed in claim 1, namely 1-allyl-1-hydroxy-1,2,5,7-tetrahydro-4H-pyrano[3,4-f]indolizino[1,2-b]-quinoline-2,5-dione.

3. A compound as claimed in claim 1, namely 1-hydroxy-1-propargyl-1,2,5,7-tetrahydro-4H-pyrano[3,4-f]indolizino[1,2-b]-quinoline-2,5dione.

4. A compound as claimed in claim 1, namely 1-benzyl-1-hydroxy-1,2,5,7-tetrahydro-4H-pyrano[3,4-f]indolizino[1,2-b]-quinoline-2,5-dione.

* * * * *